United States Patent
Tseng

(10) Patent No.: US 6,549,278 B2
(45) Date of Patent: Apr. 15, 2003

(54) CONTAMINANT INSPECTING DEVICE WITH MULTI-COLOR LIGHT SOURCE

(75) Inventor: Wen Nan Tseng, Kaohsiung (TW)

(73) Assignee: Hannstar Display Corp. (TW)

( * ) Notice: Subject to any disclaimer, the term of this patent is extended or adjusted under 35 U.S.C. 154(b) by 0 days.

(21) Appl. No.: 09/991,787

(22) Filed: Nov. 26, 2001

(65) Prior Publication Data

US 2002/0063861 A1 May 30, 2002

(30) Foreign Application Priority Data

Nov. 28, 2000 (TW) .................................. 89125426 A

(51) Int. Cl.[7] ............................................... G01N 21/00
(52) U.S. Cl. ........................ 356/237.2; 356/237.1; 356/239.1; 356/239.2; 356/239.8
(58) Field of Search ........................... 356/237.1, 237.2, 356/237.3, 237.4, 237.5, 237.6, 239.1, 239.2, 239.7, 239.8, 600; 362/234, 244, 522; 35/13

(56) References Cited

U.S. PATENT DOCUMENTS

| | | | | |
|---|---|---|---|---|
| 4,223,453 A | * | 9/1980 | Meyer | ........................... 35/13 |
| 5,085,511 A | * | 2/1992 | Grisel | ...................... 356/239.1 |
| 5,245,409 A | * | 9/1993 | Tobar | .......................... 356/600 |
| 5,666,199 A | * | 9/1997 | Hess et al. | ................. 356/239.1 |
| 6,183,108 B1 | * | 2/2001 | Herold | ........................ 362/244 |
| 6,352,359 B1 | * | 3/2002 | Shie et al. | ................... 362/522 |
| 6,379,025 B1 | * | 4/2002 | Mateescu et al. | ........... 362/239 |

FOREIGN PATENT DOCUMENTS

JP 61 284 647 * 12/1986

\* cited by examiner

*Primary Examiner*—Frank G. Font
*Assistant Examiner*—Sang H. Nguyen

(57) ABSTRACT

A contaminant inspecting device with multi-color light source comprises a support, a house mounted on the support, a transparent cover mounted on the house, a rotatable frame pivotally connected to the house, a plurality of varied color filters mounted on the frame, and a light source deposited within the house The light of the light source goes though the filter for transforming into a specific color light, and then the specific color light through the transparent cover is projected out of the house. The present invention further provides an inspecting method of the surface of the back light module using the multi-color light projected from the contaminant inspecting device with multi-color light source.

9 Claims, 2 Drawing Sheets

CONTAMINANT INSPECTING DEVICE WITH MULTI-COLOR LIGHT SOURCE

BACKGROUND OF THE INVENTION

1. Field of the Invention

The present invention generally relates to a inspecting device with a light source, and more particularly to a contaminant inspecting device with a multi-color light source for manufacturing a liquid crystal display device.

2. Description of the Related Art

With advantages of miniaturizing computer, real-time processing of operation and image, enlarging capacity of memory, increasing speed of data transmission and the like, new requirements from customer are generated, such as miniaturizing monitor of the computer for fitting a limited space, displaying and identifying of the image of the security system, and displays having little radiating and harmless features The above mentioned requirements can be met by making use of the liquid crystal display (LCD) as the interface between humans and machines. By the way, the LCDs still have the advantage of low power consumption, saving energy, portability, high resolution, and continue displaying, and thus the LCD will be an ideal and desired product in the 21st century.

The manufacturing of the LCD substantially includes injecting the liquid crystal material into a gap formed between two glass substrates with glass electrodes and attaching the polarizing films on the outside surfaces of the two glass substrates, and thus the liquid crystal display panel can be produced. Then the drive circuits, control circuits, and back light module are attached, and consequently the LCD can be made.

Generally, in the process of manufacturing the LCD, the contaminant on the surface of the back light modules, such as particulates, dusts and scratches, must be inspected out, or the LCD will be an irregular product. The conventional inspecting process of the LCD includes lighting the back light module, disposing the LCD on a table in a clean room, and inspecting the LCD directly by the sight of the operator to find out the contaminants, dusts and scratches on the LCD backlight modules and panels.

However, in the inspecting process, the operator has to look at the light source (i.e. the back light source), and therefore, the task of inspecting is relatively eye-consuming for the operators. The process is not only difficult to inspect out the contaminants and the scratches (for example, point-like contaminants and scratches with diameters larger than 0.2 mm and line-like contaminants and scratches with widths larger than 0.05 mm shall be inspected out), but also easy to misjudge when the operators' eyes are tired. The undesired contaminants and scratches will not be completely inspected out, thereby resulting in irregular products.

Accordingly, there exist needs for improving the process of manufacturing the LCD to reduce the eye tiredness of the operator during the process for inspecting the contaminants and scratches, and further increasing the yield.

SUMMARY OF THE INVENTION

It is a primary object of the present invention to provide a contaminant inspecting device with multi-color light source for inspecting the contaminants and scratches on the surface of the back light modules.

It is another object of the present invention to provide an inspecting method for inspecting the surface of the back light modules by means of the varied color light projected from the contaminant inspecting device with multi-color light source, in which the varied color light is generally parallel to and illuminates the surface of the back light module, and thus the operator may not directly stare at the surface of the back light module during inspecting the contaminants and scratches on the back light modules, thereby reducing the occupational disease of the eyes for the operators and the misjudgments resulted from eye fatigue.

In order to achieve the objects mentioned hereinabove, the present invention provides a contaminant inspecting device with multi-color light source comprising a support, a house mounted on the support, a transparent cover mounted on the house, a rotatable frame pivotally connected to the house, a plurality of varied color filters mounted on the frame, and a light source deposited within the house. The light of the light source goes though the filter for transforming to a specific color light, and then the specific color light through the transparent cover is projected out of the house.

In a preferable embodiment, the height of the support is adjustable for adjusting the height of the house.

In another preferable embodiment, the house is pivotally connected to the support such that the house can be swung relative to the support for changing the projecting angle of the specific color light. Preferably, this embodiment is further provided with an elevation angle adjusting knob for adjusting the angle of the house relative to the support.

Besides, the contaminant inspecting device with multi-color light source is preferably provided with a driving device mounted on the house to drive the rotatable frame rotating relative to the house.

The present invention further provides a method for inspecting the surface of the back light module using the contaminant inspecting device with multi-color light source. The inspecting method comprises the steps of: disposing the inspecting device on one side of the back light module, adjusting the specific color light to substantially and parallel projecting on the surface of the back light, thereby inspecting out the contaminants, the dusts and the scratches on the surface of the back light module.

Since the multi-color light projected from the device is generally parallel illuminates the surface of the back light module, the operator may not directly stare at the surface of the back light module during inspecting the contaminants and scratches on the back light modules, thereby reducing the occupational disease of the eyes for the operators and the misjudgments resulted from fatigue. Besides, the varied reflected light will be generated from the contaminants and scratches on the back light modules due to illuminating of the varied wavelength of the light, and the operator can easily inspect out the contaminants and scratches on the back light modules, thereby substantially reducing the misjudgments of the operator and improving the yield.

BRIEF DESCRIPTION OF THE DRAWINGS

Other objects, advantages, and novel features of the invention will become more apparent from the following detailed description when taken in conjunction with the accompanying drawings.

DESCRIPTION OF THE PREFERRED EMBODIMENT

Figure 1:
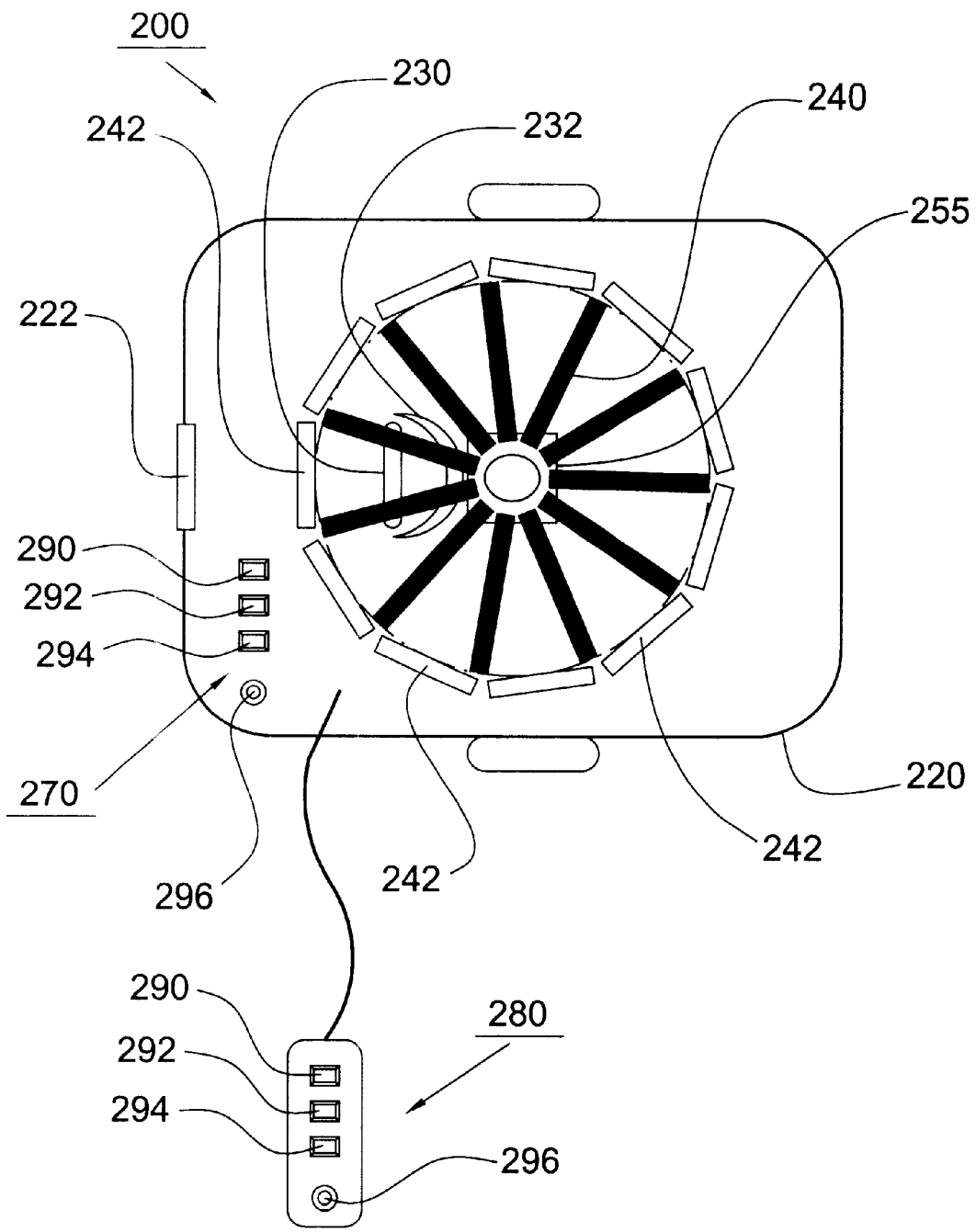
FIG. 1 is a cross sectional schematic view of a contaminant inspecting device with a multi-color light source according to an embodiment of the present invention.
Figure 2:
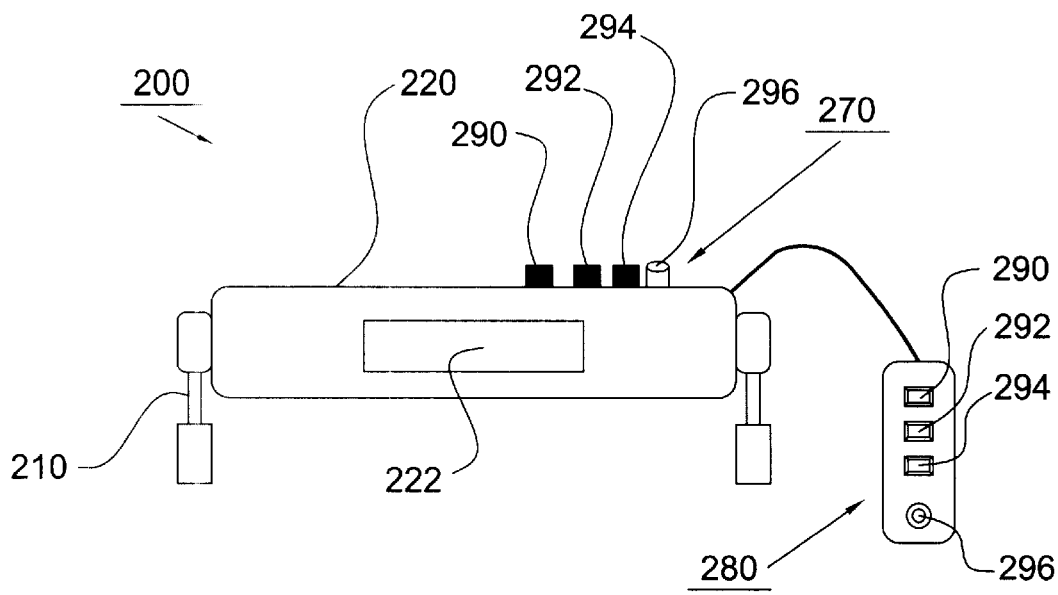
FIG. 2 is a front schematic view of the contaminant inspecting device with the multi-color light source shown in FIG. 1.

Now referring to FIGS. 1 and 2, that depict an inspecting device 200 with a multi-color light source according to a preferable embodiment of the present invention, and the inspecting device 200 can be used to inspect out the irregular products, such as the back light module of a liquid crystal display (LCD) with contaminants and scratches. While the present invention will now be described more fully hereinafter with the inspecting process of the contaminants and scratches on the back light module by way of an example, it should be noted that the inspecting device according to the present invention which can be used for the process of inspecting other surfaces will not be limited thereto.

Referring to FIGS. 1 and 2, the inspecting device 200 with a multi-color light source generally includes a support 210 and a house 220 mounted on the support 210.

The support 210 is preferably a support of which the height is adjustable thereby allowing the height of the house 220 to be adjustable. The house 220 is provided with a light source 230 and a rotatable frame 240 pivotally connected to the house 220. The rotatable frame 240 is provided with a plurality of color filters 242 with various colors. The light source 230 is preferably a high luminance halide light. As shown in the drawings, the light beam of the light source 230 goes through a refractor 232 and the color filters 242 and transforms to a specific color light with a specific wavelength, and then the specific color light through a transparent cover 222 (e.g. a plan crystal glass) mounted on the house 220 is projected out of the house 220.

Figure 3:
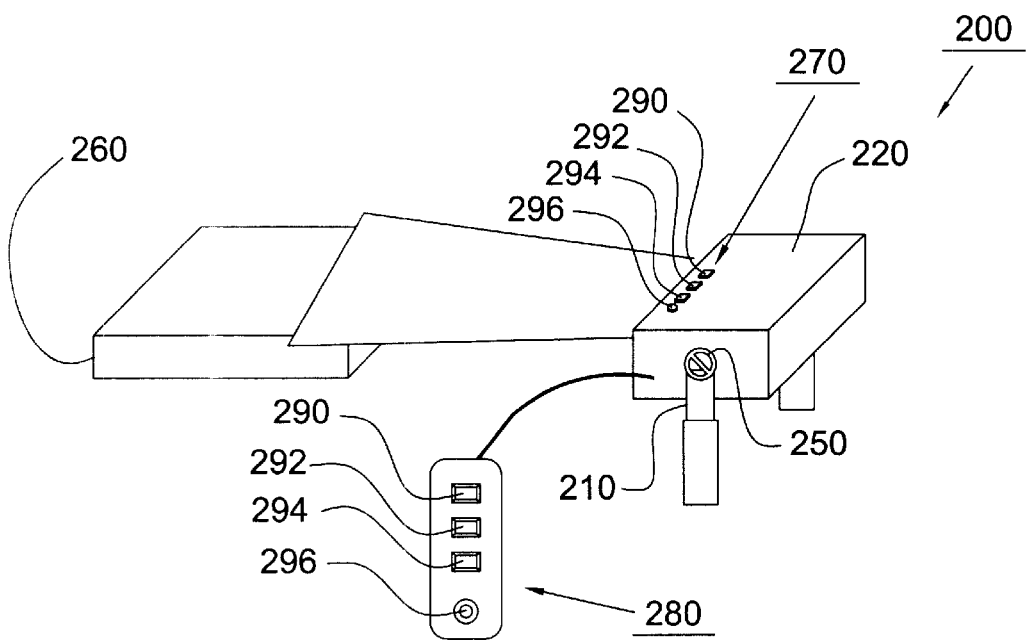
FIG. 3 is a schematic view for illustrating a method of inspecting a surface of a back light module by mean of using the contaminant inspecting device with the multi-color light source shown in FIG. 1.

Referring to FIG. 3, in the inspecting device 200 with a multi-color light source according to the present invention, the house 220 is preferably pivotally connected to the support 210 so as to swing the house 220 relative to the support 210, thereby changing the projecting angle of the specific color light. Besides, an elevation angle adjusting knob 250 is preferably provided and is used to adjust the angle of the house 220 relative to the support 210.

Further referring to FIG. 3, an inspecting method of the back light nodule according to the present invention utilizes the multi-color light projected out of the inspecting device 200 in order to inspect the surface of the back light module 260. Firstly, the inspecting device 200 with a multi-color light source is disposed on one side of the back light module 260, and then adjusting the specific color light to illuminate generally parallel to the surface of the back light 260, thereby inspecting out the contaminants, the dusts and the scratches on the surface of the back light module 260. It will be appreciated that the projecting angle and height of the specific color light can be suitably adjusted and controlled by the elevation angle adjusting knob 250 and the height adjustable support respectively.

The inspecting device 200 with a multi-color light source preferably further comprises a driving device (e.g. electrical motor 255) mounted on the house 220 for driving the rotatable frame 240 rotating relative to the house 220. Preferably, the color change and the change frequency of the light projected from the inspecting device 200 can be controlled by means of a set of function key 270, and for convenient operation the external wire-control function key 280 can be attached for controlling.

After an electrical power is turned on when a operator needs to operate the inspecting device 200 with a multi-color light source according to the present invention, the operator can push the automatic button 292 to enter the automatic mode, or push the manual button 294 to enter the manual mode. When the automatic button 292 is pushed, the driving device starts to drive the rotatable frame 240 rotating relative to the house, and the color filters 242 can be rapidly changed for generating a variety of color and wavelength light. At this time, the change frequency of the color filter 242 can be controlled by a frequency knob 296 thereby controlling the change frequency of the color of the light projected form the device 200. When the manual button 294 is pushed, and then each pushing will allow the color filters to be changed once. At this time, the change frequency of the color of the light projected form the device 200 is depended on the pushing frequency of the button.

Now referring to FIG. 3, since the multi-color light projected form the device 200 is generally parallel to and illuminates on the surface of the back light module 260, the operator may not directly stare at the surface of the back light module during inspecting the contaminants and scratches on the back light modules, thereby reducing the occupational disease of the eyes for the operator and the misjudgments resulted fatigue. Besides, the varied reflected light will be generated by the contaminants and scratches on the back light modules due to illuminating of the varied wavelength of the light, and the operator can easily inspect out the contaminants and scratches on the back light modules thereby substantially reducing the misjudgments of the operator and improving the yield.

Although the invention has been explained in relation to its preferred embodiment, it is to be understood that many other possible modifications and variations can be made without departing from the spirit and scope of the invention as hereinafter claimed.

What is claimed is:

1. A contaminant inspecting device with multi-color light source for inspecting a back light module, that is disposed on a substantially horizontal surface, for contaminants, said device comprising:
   a support disposed on the substantially horizontal surface;
   a house mounted on the support;
   a transparent window formed on a wall of the house;
   a rotatable frame pivotally connected to the house;
   a plurality of different color filters mounted on the frame; and
   a light source disposed within the house;
      wherein light generated by the light source goes through at least one of the filters for conversion to specific color light, and then the specific color light, through the transparent window, is projected out of the house and substantially parallel to the substantially horizontal surface.

2. A contaminant inspecting device with multi-color light source as claimed in claim 1, wherein the height of the support is adjustable.

3. A contaminant inspecting device with multi-color light source as claimed in claim 1, wherein the house is pivotally connected to the support such that the house can be swung relative to the support.

4. A contaminant inspecting device with multi-color light source as claimed in claim 3, further comprising an elevation angle adjusting knob for adjusting the angle of the house relative to the support.

5. A contaminant inspecting device with multi-color light source as claimed in claim 3, further comprising a driving device mounted on the house to drive the rotatable frame rotating relative to the house.

6. A contaminant inspecting device with multi-color light source as claimed in claim 5, wherein the driving device is a motor.

7. A contaminant inspecting device with multi-color light source as claimed in claim 1, wherein the frame, the light source and the window are positioned generally on a plane, and the frame is rotatable in said plane to pass the filters between the light source and the window.

8. A contaminant inspecting device with multi-color light source as claimed in claim 7, wherein the window is elongated in a direction generally parallel to said plane.

9. A method of inspecting a surface of a back light module for at least one of dusts, scratches, and contaminants, using specific color light projected from a contaminant inspecting device with a multi-color light source, which device comprises a support, a house mounted on the support, a transparent window formed on a wall of the house, a rotatable frame pivotally connected to the house, a plurality of varied color filters mounted on the frame, and a light source deposited within the house, wherein light generated by the light source goes through at least one of the filters for conversion to the specific color light, and then the specific color light, through the transparent window, is projected out of the house, the method comprising the steps of:

disposing the contaminant inspecting device on one side of the back light module; and adjusting the specific color light to illuminate the surface of the back light module in a direction generally parallel to the surface to inspect the surface of the back light module for said at least one of dusts, scratches, and contaminants.

* * * * *